(12) United States Patent
Liu et al.

(10) Patent No.: US 8,537,353 B2
(45) Date of Patent: Sep. 17, 2013

(54) SENSOR CHIP FOR BIOLOGICAL AND CHEMICAL SENSING

(75) Inventors: Hong Liu, Singapore (SG); Xiaodong Zhou, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 392 days.

(21) Appl. No.: 12/991,070

(22) PCT Filed: Apr. 30, 2009

(86) PCT No.: PCT/SG2009/000156
§ 371 (c)(1),
(2), (4) Date: Feb. 1, 2011

(87) PCT Pub. No.: WO2009/136869
PCT Pub. Date: Nov. 12, 2009

(65) Prior Publication Data
US 2011/0116093 A1    May 19, 2011

Related U.S. Application Data

(60) Provisional application No. 61/050,495, filed on May 5, 2008.

(51) Int. Cl.
*G01J 3/00* (2006.01)
*G01N 21/55* (2006.01)

(52) U.S. Cl.
USPC .......................................... 356/300; 356/445

(58) Field of Classification Search
USPC ..... 356/237.1–241.6, 242.1–243.8, 426–431, 356/600–640
See application file for complete search history.

(56) References Cited

U.S. PATENT DOCUMENTS

| | | | | |
|---|---|---|---|---|
| 3,135,867 | A * | 6/1964 | Daneff | 356/431 |
| 4,218,144 | A * | 8/1980 | Whitehouse et al. | 356/446 |
| 4,570,074 | A * | 2/1986 | Jette | 250/559.49 |
| 4,675,730 | A * | 6/1987 | Adomaitis et al. | 348/131 |
| 4,724,481 | A * | 2/1988 | Nishioka | 348/133 |
| 5,068,799 | A * | 11/1991 | Jarrett, Jr. | 702/40 |
| 5,440,648 | A * | 8/1995 | Roberts et al. | 382/141 |
| H1616 | H * | 12/1996 | Wolfe | 348/88 |
| 5,642,198 | A * | 6/1997 | Long | 356/430 |
| 5,696,591 | A * | 12/1997 | Bilhorn et al. | 356/429 |
| 6,750,466 | B2 * | 6/2004 | Guha et al. | 250/559.46 |
| 8,084,260 | B2 * | 12/2011 | Gunstream et al. | 436/8 |

* cited by examiner

*Primary Examiner* — Gregory J Toatley
*Assistant Examiner* — Jarreas C Underwood
(74) *Attorney, Agent, or Firm* — Moser Taboada

(57) ABSTRACT

A sensor chip comprising:
a micro/nanofluidic channel;
at least one nanostructure provided in said channel along an optical path for the transmission of a light beam;
a light transparent element disposed along the optical path and arranged to allow transmission of light onto said nanostructure; and
a non-transparent element surrounding at least a portion of said optical path to at least partially reduce light scatter from the optical path.

18 Claims, 11 Drawing Sheets

SENSOR CHIP FOR BIOLOGICAL AND CHEMICAL SENSING

TECHNICAL FIELD

The present invention generally relates to a sensor chip, a process for making said sensor chip and a method for using said sensor chip for localized surface plasmon resonance detection.

BACKGROUND

Biosensors have been exploited by researchers for many years in the areas of diagnostics and monitoring of diseases, drug discovery, proteomics and environmental monitoring. Fundamentally, biosensors are analytical devices that convert a biological response into a detectable electrical or optical signal. A large amount of biosensor research efforts have been devoted to the evaluation of the relative merits of various signal transduction methods such as optical, radioactive, electrochemical, piezoelectric, magnetic and micromechanical.

One of the known signal transduction devices used for biological applications includes optical spectroscopic devices, such as Surface Plasmon Resonance (SPR) devices, which provide a label-free, real-time measurement of a substance by using an optical method that detects changes in the refractive index of a dielectric film adjacent to a metal surface. However, in the era of nano-scale research, the use of SPR for nano-scale biological applications is particularly limited. A variety of auxiliary optical structures are usually required to induce SPR (including a prism, grating, or waveguides). In this regard, due to the difficulties involved in assembling these auxiliary optical structures in a miniaturized scale, known miniaturized SPR devices do not usually have an integrated conduit for the liquid sample. Accordingly an independent flow cell has to be used. This results in a constant need to arduously align the flow cell with the miniaturized SPR devices before each operation.

In view of the above, the ability of localized surface plasmon resonance (LSPR) spectroscopy to be employed in biological applications is increasingly important and has been demonstrated by several research groups. The phenomenon of localized surface plasmon resonance is caused by certain unique properties of noble metal nanoparticles. Noble metal nanoparticles exhibit a strong UV-visible absorption band that is absent in the spectrum of the bulk noble metal. This absorption occurs when the incident photon frequency is resonant with the collective oscillation of the conduction electrons in the nano-metal particles, resulting in LSPR. Similar to SPR which is already widely used by biologists, LSPR is also an effective tool to characterize the biological interfaces, and has ten times higher sensitivity than SPR within its electromagnetic decay length of 5-15 nm. This makes LSPR quite suitable for monolayer molecular or short-chain DNA detection.

As compared to SPR, which utilizes a noble metal film and requires auxiliary optical structures (either prism, gratings, or waveguides) for it to function, LSPR can easily be measured through a normal UV-vis-near-IR spectroscopy, by the absorption spectrum of noble metal (silver or gold) nanostructures. Furthermore, the peak of the LSPR spectrum is tunable according to the shape and size of the metal nanostructures.

Currently LSPR has been confined to applications involving laboratory research. Known methods used in the fabrication of micro/nanofluidic devices are not suitable for LSPR device fabrication. For example, the use of anodic bonding at high temperatures may damage the nanostructures, which are important components required for LSPR generation. Moreover, the glass etching technique, which is commonly used in micro/nanofluidic device fabrication, will roughen the surface of the glass wafers and cause a lot of unwanted scatterings in LSPR.

There is a need to provide a sensor chip that overcomes, or at least ameliorates one or more of the disadvantages described above.

There is a need to provide a sensor chip for detecting LSPR on a miniaturized scale, that would meet any one or more of the following criteria: is biocompatible, robust, cost-effective, transparent with minimum light scatterings, has an integrated conduit that contains the fluid sample and can be fabricated through mass production.

SUMMARY

According to a first aspect, there is provided a sensor chip comprising:
a micro/nanofluidic channel;
at least one nanostructure provided in said channel along an optical path for the transmission of a light beam;
a light transparent element disposed along the optical path and arranged to allow transmission of light onto said nanostructure; and
a non-transparent element surrounding at least a portion of said optical path to at least partially reduce light scatter from the optical path.

In one embodiment, the transparent element of the first aspect is comprised of silicon-based material. In one embodiment, the silicon-based material is silica.

Advantageously, the silicon-based material is chosen such that optical scattering is minimized.

In one embodiment, the sidewalls of the sensor chip are comprised of a layer of non-transparent silicon disposed between a layer of silicon dioxide and a transparent layer of glass. Advantageously, the silicon dioxide and a layer of glass may be coupled together by a cured polymer.

According to a second aspect, there is provided a localized surface plasmon resonance sensor chip comprising:
a micro/nanofluidic channel;
at least one nanostructure provided in said channel along an optical path for the transmission of a light beam from a light source;
a light transparent element disposed along the optical path and arranged to allow transmission of light onto said nanostructure; and
at least one non-transparent element surrounding at least a portion of said optical path to at least partially reduce light scatter from the optical path;
wherein in use, a light beam is passed through said optical path and over said nanostructure to produce a localized surface plasmon resonance signal.

In one embodiment, there is provided a localized surface plasmon resonance sensor chip comprising:
a micro/nanofluidic channel having a base surrounded by sidewalls, said sidewalls comprising a layer of non-transparent silicon disposed between a silicon dioxide layer adjacent to the base and a glass layer;
a plurality of nanostructures provided in said base capable of producing localized surface plasmon resonance when illuminated by light at an incident angle; and
a glass layer provided over said channel adjacent said glass layer of said side walls for allowing light to be transmitted therethrough and onto said nanostructures According to a third aspect, there is provided a localized surface plasmon resonance system comprising:

a source of light;

a sensor chip comprising: a micro/nanofluidic channel; at least one nanostructure provided in said channel along an optical path for the transmission of light beam from the light source to produce a localized surface plasmon resonance signal; a pair of light transparent elements disposed along the optical path and having the nanostructure located therebetween; and at least one non-transparent element surrounding at least a portion of said optical path to at least partially reduce light scatter from the optical path; and a detector disposed along the optical path for detecting the localized surface plasmon resonance signal.

According to a fourth aspect, there is provided a process for making a sensor chip comprising the steps of:

joining a first substrate and a second substrate together, the first substrate having at least one nanostructure thereon and the second substrate being configured to form a micro/nanofluidic channel between said first and second substrate, said second substrate having an optical path to allow transmission of light onto said nanostructure; and mounting a light transparent element along said optical path to allow transmission of light onto said nanostructure.

In one embodiment, there is provided a process of the fourth aspect, comprising the step of:

etching the second substrate to form sidewalls.

In one embodiment, there is provided a process of the fourth aspect, comprising the step of:

providing the second substrate having a layer of silicon dioxide and a layer of glass.

The process may comprise the step of:

providing on the second substrate, a layer of non-transparent silicon between the silicon dioxide and glass layers. Advantageously, the non-transparent silicon layer is capable of at least partially reducing light scatter from the optical path to improve the LSPR signal to noise ratio.

In one embodiment, there is provided a process of the fourth aspect further comprising the step of providing a non-transparent element adjacent to said first substrate to at least partially reduce light scatter from the optical path. In one embodiment, the step of providing a non-transparent element comprises disposing a metal layer on the first substrate to form an optical opening on one side of the substrate prior to the nanostructure fabrication. Advantageously, the metal layer which forms an optical opening on the substrate enhances the signal to noise ratio as well as the contrast of the LSPR signal.

In another embodiment, there is provided a process of the fourth aspect, wherein the nanostructure is disposed on the first substrate by nanosphere lithography (NSL).

According to a fifth aspect, there is provided a method of using the sensor chip of the first aspect, the method comprising the steps of:

directing a light beam from a light source through the optical path and incident on said nanostructure;

contacting a fluid sample with said nanostructure while light is being incident thereon;

detecting the light reflected or transmitted from said nanostructure while in contact with said fluid sample; and measuring the characteristics of said reflected or transmitted light to determine the localized surface plasmon resonance associated with the fluid sample.

DEFINITIONS

The following words and terms used herein shall have the meaning indicated:

The term "channel" as used herein is to be interpreted in a broad sense. Thus, the term "channel" is not intended to be restricted to elongated configurations where the transverse or longitudinal dimension greatly exceeds the diameter or cross-sectional dimension. Rather, the term is meant to include a conduit of any desired shape or configuration through which liquids may be directed. A channel may be filled with one or more sample fluids to be analysed in a detection method such as localized surface plasmon resonance.

The term "microfluidic" in the context of this specification, refers to, without any restriction, a channel through which fluid(s) are capable of being passed or directed, wherein one or more of the dimensions of the channel are in the range between about 1 micron and about 1500 microns.

The term "nanofluidic" in the context of this specification, refers to, without any restriction, a channel through which fluid(s) are capable of being passed or directed, wherein one or more of the dimensions of the channel are less than about 1 micron. Hence, the term "micro/nanofluidic" is a collective term and refers to a microfluidic channel or a nanofluidic channel.

The term "transparent" refers to any substance that allows light easily pass through such that objects placed on the back can be fully seen through the substance.

The term "transparent element" refers to any object that is formed of material that has the property of being transparent as defined above. For example, a transparent element may be the sidewall of a micro/nanofluidic channel.

The term "non-transparent" refers to any substance that is not transparent in that it does not permit light to easily pass therethrough such that objects placed on the back can not be fully seen through the substance. Accordingly, the term does not exclude substances that may be partially transparent, such as for example a material that is translucent.

The term "non-transparent element" refers to any object that is formed of material that has the property of being non-transparent as defined above. For example, a non-transparent element may be the sidewall of a micro/nanofluidic channel.

The term "fluid sample" as used herein is to be interpreted broadly to include any fluid material or mixture of fluid materials that contains one or more components of interest for a localized surface plasmon resonance analysis. The fluid material or mixture of fluid materials can either be in a liquid phase or a gaseous phase. The fluid sample may be a biological sample, a biochemical sample or a chemical sample. The fluid sample may be undergoing a reaction during the detection process. The reaction may include rigid or viscoelastic layer film formation, film layer removal, affinity binding, ligand-receptor binding, competitive binding and chemical reaction. Exemplary chemical reactions occurring in the fluid sample which may be measured include coupling of amino group functionalized molecules, macromolecules or particles to a carboxylic group terminated surface via an active ester intermediate (EDC/NHS coupling for aqueous condition and DCC/NHS coupling for non-aqueous condition), esterification polymerization and photo-polymerization of the components within said fluid sample.

The term "nanostructures" as used herein is to be interpreted broadly to include free-standing or isolated three dimensional structures from the base of the micro/nanochannel which have at least two dimensions that are less than about 1 µm, more typically 20 nm to 800 nm.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DISCLOSURE OF EMBODIMENTS

Exemplary, non-limiting embodiments of a sensor chip for use in chemical and biological sensing techniques such as localized surface plasmon resonance, will now be disclosed.

The sensor chip comprises a micro/nanofluidic channel;

at least one nanostructure provided in said channel along an optical path for the transmission of a light beam;

a light transparent element disposed along the optical path and arranged to allow transmission of light onto said nanostructure; and a non-transparent element surrounding at least a portion of said optical path to at least partially reduce light scatter from the optical path.

In one embodiment, the sensor chip comprises a single nanostructure. The sensor chip may also comprise a plurality of nanostructures.

In one embodiment, at least one of the nanostructure is a metal. The metal may be selected from the group consisting of Group IB, Group VIB, Group VIIIB, Group IVA, Group IVB, Group IIB and Group IIIA of the Periodic Table of Elements, as well as their alloys and combinations thereof.

The nanostructure may also be a noble metal. In another embodiment, at least one of the nanostructure is a metal selected from the group consisting of gold, aluminum, cobalt, indium, molybdnenum, nickel, palladium, platinum, tin, titanium, tungsten, zinc, silver, copper and combinations thereof. In one embodiment, the nanostructure is a gold nanostructure. In another embodiment, when a plurality of nanostructures is present, the nanostructures may be a mixture of the different metals disclosed above.

Desirably, the nanostructure may be non-reactive to the solvent within the fluid sample and may be non-reactive to oxygen, water, methanol, ethanol and the like. The nanostructures may be substantially three-dimensional. The nanostructure may be substantially regular or irregular in shape. The cross-section of the nanostructure may be substantially circular, triangular, rectangular, rhombic, ellipsoid or squarish.

In one embodiment when the nanostructure has substantially circular cross-section, the diameter of the nanostructure may range from about 20 nanometers to about 800 nanometers, from about 30 nanometers to about 800 nanometers, from about 40 nanometers to about 800 nanometers, from about 50 nanometers to about 500 nanometers, from about 100 nanometers to about 400 nanometers, from about 100 nanometers to about 300 nanometers, from about 100 nanometers to about 200 nanometers, from about 200 nanometers to about 500 nanometers and from about 300 nanometers to about 500 nanometers. In another embodiment, when the nanostructure has rectangle or square cross-section, the lengths and breadth of the rectangle or square cross-sections may range from about 20 nanometers to about 800 nanometers, from about 30 nanometers to about 800 nanometers, from about 40 nanometers to about 800 nanometers, from about 50 nanometers to about 500 nanometers, from about 100 nanometers to about 400 nanometers, from about 100 nanometers to about 300 nanometers, from about 100 nanometers to about 200 nanometers, from about 200 nanometers to about 500 nanometers and from about 300 nanometers to about 500 nanometers.

In one embodiment, the nanostructure is selected from the group consisting of disks, cubes, cylinders and spheres. When a plurality of nanostructures is used, the arrangement of the nanostructures on the first substrate may be random, patterned, periodic or ordered. The nanostructure may be attached on the channel individually or in bulk. Adhesive means may be utilized to attach the nanostructure on the base of the channel. The nanostructure may be disposed on the base of the channel by direct deposition methods or lithographic methods. In one embodiment, the nanostructure is disposed on the first substrate by nanosphere lithography (NSL). When there is a plurality of nanostructures, the nanostructures may be separated from each other by a distance of ranging from about 1 nanometer to about 50000 nanometers, from about 50 nanometers to about 50000 nanometers, from about 100 nanometers to about 40000 nanometers, from about 100 nanometers to about 30000 nanometers, from about 100 nanometers to about 20000 nanometers, from about 200 nanometers to about 10000 nanometers, from about 200 nanometers to about 5000 nanometers, from about 300 nanometers to about 5000 nanometers. In one embodiment, a single nanostructure is disposed on said first substrate.

The nanostructure may also be functionalized with chemical groups such as hydroxyl groups, carboxylic amide groups, and short alkyl chains (e.g., 1-6 carbons) with terminal hydroxyl or carboxylic amide groups. Target biomolecules such as receptors, ligands and any other biomolecules of interest may also be functionally attached to the nanostructures.

The base of the channel may have at least a portion that is opaque, translucent or transparent. In one embodiment, the base of the channel is comprised of inorganic silica-based material. The base of the channel may be glass. The base of the channel may also be biocompatible and/or chemically inert. The base of the channel may be capable of contacting a fluid sample containing target analytes of interest for a long period of time without having an undesirable change in its properties; that the base is chemically and biologically inert to the fluid sample. The base of the channel may have a thickness from about 10 nanometers to about 10 centimeters.

In one embodiment, the non-transparent element forms at least part of the sidewalls of said micro/nanofluidic channel.

In another embodiment, the non-transparent element is provided in or adjacent to the base of the said micro/nanofluidic channel. In yet another embodiment, the non-transparent element may be used to coat at least one side of the first substrate to surround at least a portion of the optical path to at least partially reduce light scatter from the optical path. The non-transparent element may also be used to coat at least one side of the second substrate and/or at least a portion of the light transparent element, to thereby form an optical opening. The non-transparent element may also be used to coat at least one side of sidewalls of the channels. Advantageously, this improves the signal to noise ratio of the LSPR signal. The non-transparent element may also be within the first substrate, second substrate, and/or at least a portion of the light transparent element. In another embodiment, the non-transparent element may be an inherent feature of the first substrate, second substrate, and/or at least a portion of the light transparent element. The non-transparent element may be a layer of metal film. The metal film may be selected from the group consisting of Group IB, Group VIB, Group VIIIB, Group IVA, Group IVB, Group IIB and Group IIIA of the Periodic Table of Elements, as well as their alloys and combinations thereof. In one embodiment, the metal film may be selected from the group consisting of aluminum film, cobalt film, copper film, gold film, indium film, molybdenum film, nickel film, palladium film, platinum film, silver film, tin film, titanium film, tungsten film, zinc film and combinations thereof. In one embodiment, the metal is a gold film.

The material required to form the sidewalls of the channel may be capable of withstanding the pressure of an incoming fluid sample. The sidewalls may be made of a material that is capable of being etched to the desired shape. In one embodiment, the sidewalls are made from a silicon wafer that is coated with a layer of photoresist. The sidewalls may be a glass, silicon dioxide, silicon, silicon nitride, quartz, any other ceramics, Poly(methyl methacrylate) (PMMA), polycarbonate, Poly(Ethylene-co-Ethyl Acrylate) (PEEA), Polydimethysiloxane (PDMS) or mixtures thereof. The sidewalls may have at least a portion that is opaque, translucent or transparent. In one embodiment, the sidewalls are non-transparent to at least partially reduce light scatter from the optical path. Advantageously, this provides a higher signal to noise ratio for the LSPR signal. In another embodiment, the sidewalls of the channel are comprised of substantially transparent material, which is coated with a non-transparent element. In another embodiment, the sidewalls of the channel are comprised of silicon-based material. In yet another embodiment, the second substrate is selected from the group consisting of glass, silicon dioxide, silicon, silicon nitride, quartz, any other ceramics, Poly(methyl methacrylate) (PMMA), polycarbonate, Poly(Ethylene-co-Ethyl Acrylate) (PEEA), Polydimethysiloxane (PDMS) or mixtures thereof. The sidewalls may comprise a layer of non-transparent silicon disposed between a layer of silicon dioxide and a layer of glass. Advantageously, the non-transparent silicon is capable of reducing light scatter and improving the LSPR signal to noise ratio. The sidewalls may be capable of contacting the fluid sample for long period of time without having an undesirable change in its properties. The sidewalls may have a thickness from about 10 nm to about 1000 μm.

In one embodiment, the light transparent element is at least one of glass and polydimethysiloxane. In one embodiment, the light transparent element is a layer provided over said channel for allowing light to be transmitted through said channel and onto said nanostructures. In another embodiment, a second light transparent element is disposed along the optical path and arranged to allow transmission of light that has passed said nanostructure. The second light transparent element may form the base of the channel. In one embodiment, the second light transparent element may also be the first substrate having at least one nanostructure thereon. The light transparent element may be comprised of silicon-based material. In one embodiment, the silicon-based material is a silica-based material. In another embodiment, the silicon-based material is silica. In one embodiment, the silicon-based material has a similar refractive index to glass. In another embodiment, the silicon-based material is glass. The glass may comprise from about 60% wt to about 99% weight of silica. The glass may comprise about from 1% weight to from about 40% weight of metal oxide or metal carbonates comprising additives. In one embodiment, the glass may comprise, in addition to silica, additives selected from the group consisting of sodium oxide, sodium carbonate, magnesium carbonate, calcium oxide, lead, lanthanum, boron, boron oxide, thorium, cerium, antimony, mixtures thereof and salts thereof. In one embodiment, the glass is boro-silicate glass. In one embodiment, the glass is Pyrex 7740 glass wafer.

The light transparent element may have a similar refractive index as glass. In one embodiment, the light transparent element has a refractive index of from about 1.4 to about 2. Preferably, the transparent element has a refractive index of from about 1.45 to about 1.55. The light transparent element may have a light transmission of about 50% to about 100%. In one embodiment, the light transparent element has a light transmission of about 100%. The light transparent element may be capable of contacting the fluid sample for long period of time without having an undesirable change in its properties. The light transparent element may have a thickness from about 10 nm to about 10 mm.

In one embodiment, various parts of the sensor chip may be coupled together using a curable material. For example, the silicon dioxide and the layer of glass of the sidewalls of the channel may be coupled together by a cured polymer. Exemplary curable polymer includes epoxy compounds, polyetherimide and acrylic-based compounds. In one embodiment, the curable polymer is UV curable epoxy. In yet another embodiment, the curable material is one that has a similar refractive index to glass. When a material such as PDMS is used, the coupling of the PDMS and glass may be carried out by oxygen plasma activation.

In one embodiment, the disclosed sensor chip comprises a reflector arranged to reflect light that has passed over said nanostructure back toward the optical path. The reflector may be any material that has light reflecting properties. In one embodiment, the reflector is comprised of a metal. The reflector may be disposed on at least one side of the first substrate or the base of the channel.

The channel of the disclosed sensor chip may be coupled to at least one inlet for transmission of a fluid sample into said channel and at least one outlet for transmission of said fluid from said channel. In one embodiment, at least one portion of said channel allows light to be transmitted onto said nanostructures. The channel of the sensor chip may have at least one dimension of from about 10 nanometers to about 1000 microns.

In one embodiment, the channel has a cross-sectional shape selected from the group consisting of trapezoid, square, rectangle and circle. When the cross-section of the channel is a circle, the diameter of the channel may range from about 1 micron to about 15000 microns, from about 10 microns to 10000 microns, from about 50 microns to about 8000 microns, from about 50 microns to about 500 microns, from about 50 microns to about 5000 microns, from about 50 microns to about 2000 microns and from about 50 microns to about 1000 microns. When the cross-section of the channel is a rectangle, a square, or a trapezoid, the breadth and height of the channel may range from about 1 micron to about 15000 microns, from about 10 microns to 15000 microns, from 50 microns to about 8000 microns, from about 50 microns to about 5000 microns, from about 50 microns to about 2000 microns and from about 50 microns to about 1000 microns. In one embodiment, the channels are 100 microns wide and have a depth of 50 microns.

The disclosed sensor chip may be used with a light source which provides an incident light beam on the nanostructures to thereby generate localized surface plasmon resonance. In another embodiment a broadband source such as halogen lamp and a tunable laser source may be used. In yet another embodiment, a narrowband source such as a light emitting diode or a diode laser is used.

For the detection of LSPR, a standard spectrometer in transmission mode at any angle that is roughly normal to the sensor chip plane may be used.

A home-made or customized spectrometer may also be built for LSPR measurements.

When the broadband light source is used, after the light beam from the light source has passed through the sensor chip, the light may be transmitted to a diffraction grating and a photodiode array may be used to analyze the spectrum of the device. When a narrow light source is used, a photodetector can be used to detect the power of the specific wavelength after passing through the sensor chip as the power detected at a fixed wavelength changes when the LSPR extinction peak shifts in wavelength. Advantageously, this method of detection is more cost effective, but is suitable only when the spectra of the device are already well-characterized. In one embodiment, the sensor chip is used together with a photodetector that is capable of detecting the intensity of transmitted light from the nanostructures. In another embodiment, when a reflector or reflective layer is used on the first substrate or the bottom of the channel, the reflected light may be detected by the photodetector. The photodetector may be any device that is capable of sensing or detecting light. The light detector may be a photodetector such as a photocell, a photodiode, a phototransistor, a charge-coupled device, an image sensor, a photo-electric tube or a photomultiplier. As the light is detected, the intensity of the light transmitted/reflected from the sensor chip may be transmitted from the light detector to a computer or reader that is capable of analyzing the results and hence, generating a localized surface plasmon resonance profile.

When a light beam at a specific wavelength is used, the light beam may be in the visible light region, the infra-red region or ultra-violet region of the Electromagnetic Spectrum. The light beam may be a laser beam. The laser beam may be emitted from a laser light source. The light beam may be substantially s-polarized, substantially p-polarized or substantially unpolarized.

The wavelength of the light beam may be in the range of about 500 nm to about 1200 nm. In one embodiment, the wavelength of the light beam is about 543 nm, about 594 nm, about 633 nm or about 1150 nm.

The intensity of the light beam may be in the range of about 0.01 mW/mm$^2$ to about 100 mW/mm$^2$. In one embodiment, the intensity of the light beam in the form of a laser beam may be selected from the group consisting of about 0.014 mW/mm$^2$, about 0.029 mW/mm$^2$, about 0.057 mW/mm$^2$, about 0.0111 mW/mm$^2$, about 0.14 mW/mm$^2$, about 0.228 mW/mm$^2$, about 0.30 mW/mm$^2$, about 0.337 mW/mm$^2$, about 0.452 mW/mm$^2$ and about 0.568 mW/mm$^2$.

In one embodiment, the disclosed sensor chip is a micro/nanofluidic device. In another embodiment, the disclosed sensor chip may be used as a DNA chip, lab-on-a-chip device, Bio-micromechanical electronic system (Bio-MEMS) and biosensor. Micro-propulsion devices such as micropumps may also be incorporated in the disclosed sensor chip.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 5a shows the FESEM picture of the nanostructures at 2500× magnification while FIG. 5b shows the FESEM picture of the nanostructures at 23000× magnification.

FIG. 6a shows the LSPR spectrum for a glass-silicon-glass structure when the adjacent media of the gold nanostructures are air and water. FIG. 6b shows the LSPR spectrum for the same structure with a 3 mm thick layer of PDMS added, when the nanostructures' adjacent medium is water.

DETAILED DESCRIPTION OF FIGURES

Figure 1A:
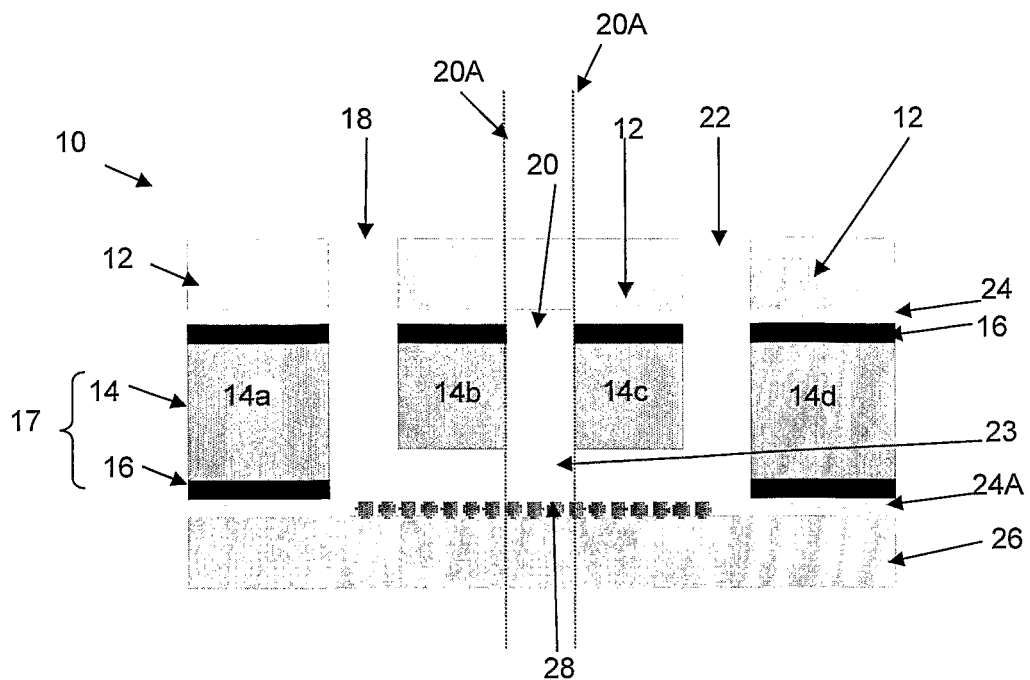
FIG. 1a is a schematic diagram of a cross-sectional view of one embodiment of a sensor chip as disclosed herein and FIG. 1b is a schematic diagram of a cross-sectional view of another embodiment sensor chip having a non-transparent element as disclosed herein.

Referring to FIG. 1a there is shown a micro/nanofluidic sensor chip 10 for detecting localized surface plasmon resonance associated with a fluid sample.

A substrate in the form of a Pyrex 7740 glass 26, forms the bottom of the micro/nanofluidic sensor chip 10. A plurality of gold nanostructures 28, having shapes suitable for LSPR application, are disposed on the glass substrate 26. A combination of a silicon dioxide layer (SiO$_2$) 16 and non-transparent silicon wafer (Si) 14 (14a-14d) collectively form the sidewall material 17 to define a micro/nanofluidic channel 23. The silicon wafer 14 is attached to the ends of the glass 26 by means of a Loctitte 3301 UV curable epoxy 24A. The sidewall material 17 is then in turn attached to a transparent inorganic layer, which is also in the form of a Pyrex 7740 glass 12, by means of the UV curable epoxy 24. The glass 12 forms the top layer of the micro/nanofluidic sensor chip 10 and is optically transparent to allow light to pass through. The glass 26, silicon dioxide layer (SiO$_2$) 16, silicon wafer (Si) 14 and glass 12 are arranged in a manner such that the silicon dioxide layer (SiO$_2$) 16 and silicon wafer (Si) 14 are sandwiched between the glass 26 and the glass 12, and the micro/nanofluidic channel 23 is a substantially enclosed chamber. The glass layer 12 and sidewall material layer 17 are discontinuous such that micro/nanofluidic channel 23 is comprised of an inlet 18, a transparent portion 20 and an outlet portion 22. Transparent channel portion 20 serves as part of an optical or light path 20A for incident light to reach the gold nanostructures 28 disposed on the glass 26. Channel 23 allows the fluid sample to flow from the inlet 18 across the gold nanostructures 28 to the outlet 22.

Figure 1B:
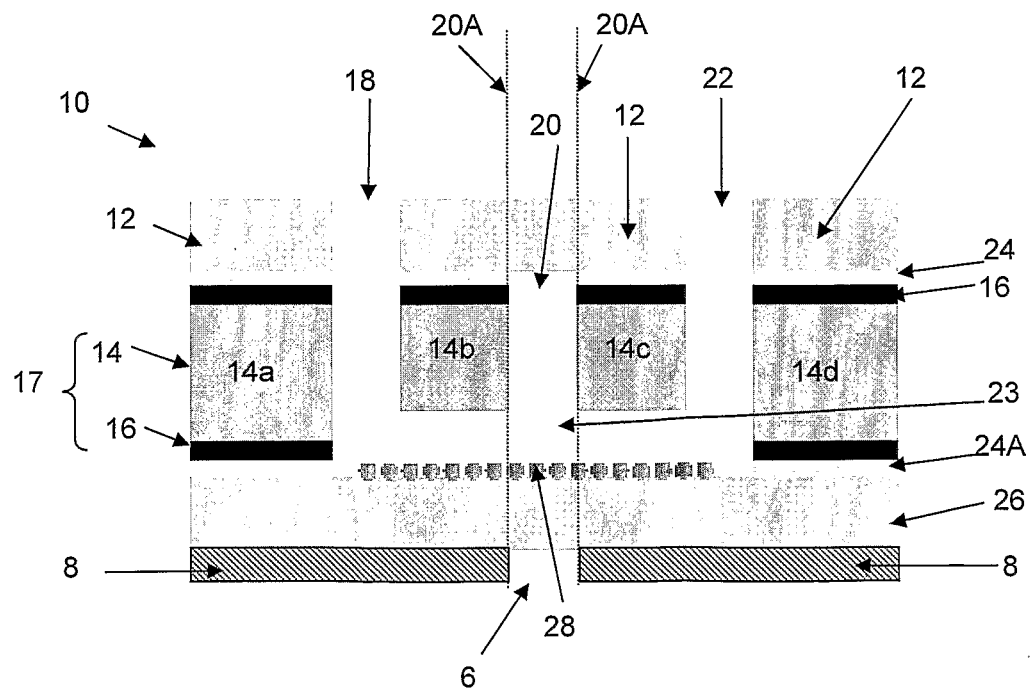

Referring now to FIG. 1b, there is shown the micro/nanofluidic sensor chip 10 of FIG. 1a having a non-transparent element in the form of a metal layer 8, on bottom side of the glass substrate 26. The layer of metal 8 may be fabricated with an optical opening 6, so as to block the light from the areas other than the sensing area (not shown), thus further enhancing the signal to noise ratio of LSPR. The silicon layer 14 (14a-14d) is also capable of blocking the visible light, but in infra-red range the silicon is transparent and hence the metal layer 8 is required to block the infra-red light from the areas other than the sensing area. It should be noted that the metal layer 8, may not be required for the sensor device if the portions of the silicon wafer 14b,14c are non-transparent to light. However, in a preferred embodiment, the metal layer 8 is used together with the non-transparent silicon layer 14.

Figure 2A:
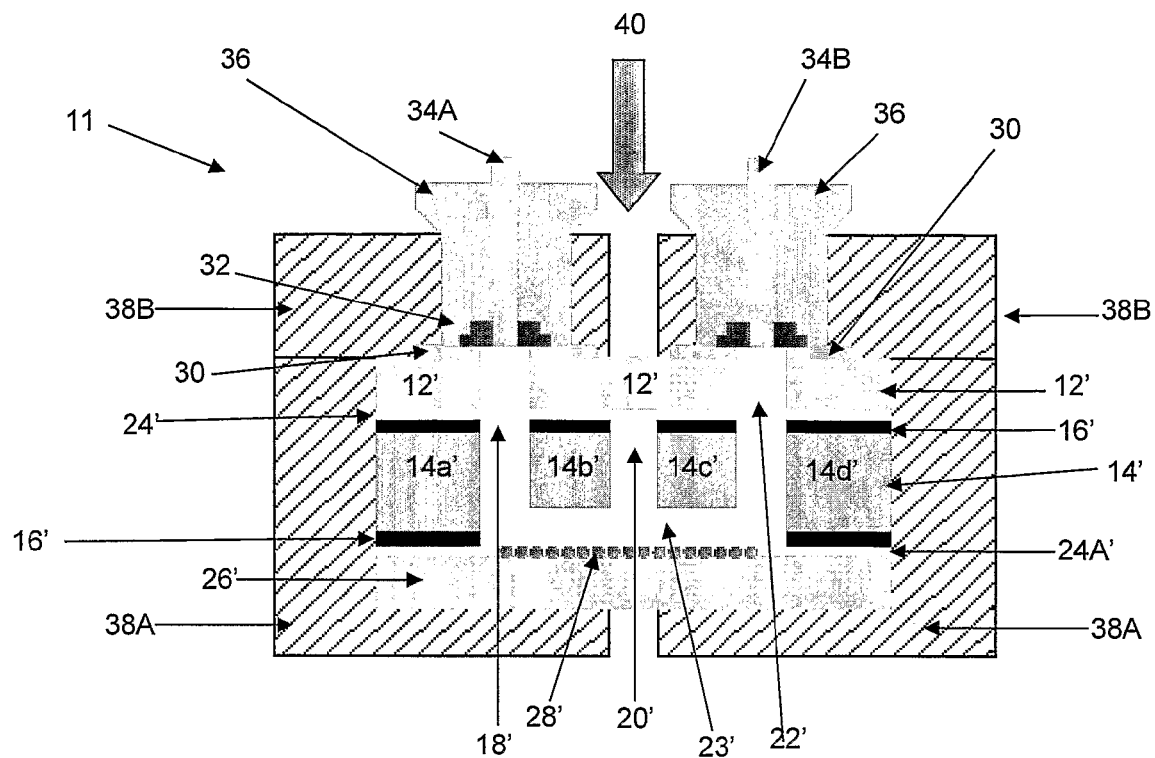
FIG. 2a is one embodiment of a schematic cross-sectional assembly view of the sensor chip being used in a localized surface plasmon resonance system.
Figure 2B:
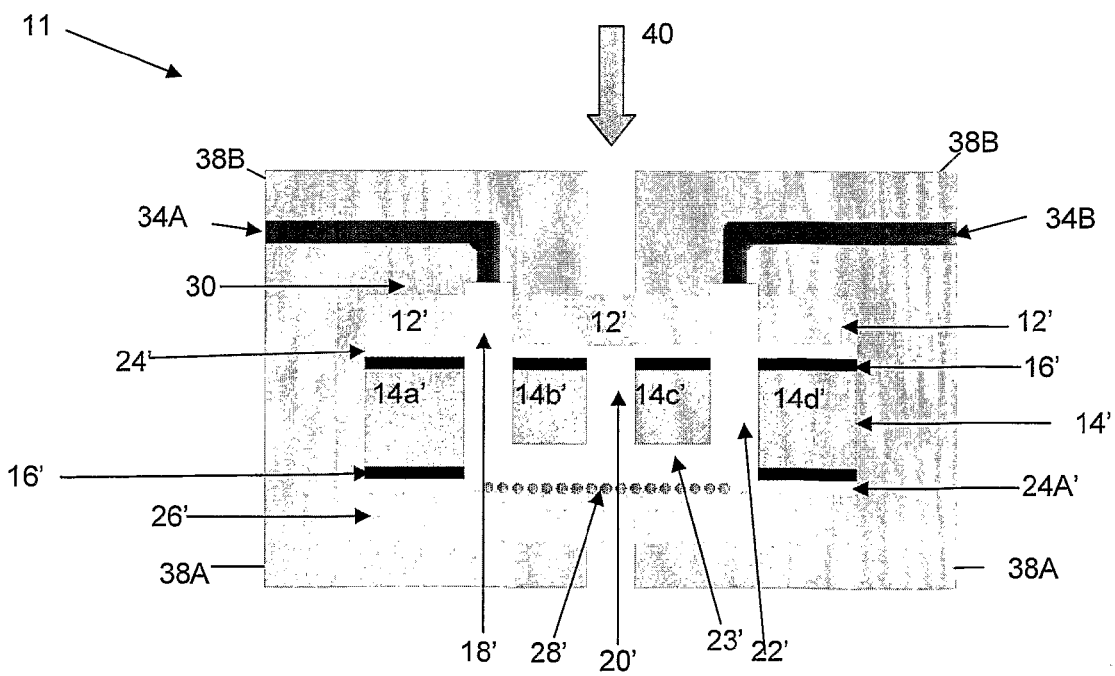
FIG. 2b is another embodiment of a schematic cross-sectional assembly view of the sensor chip being used in a localized surface plasmon resonance system.
Figure 3:
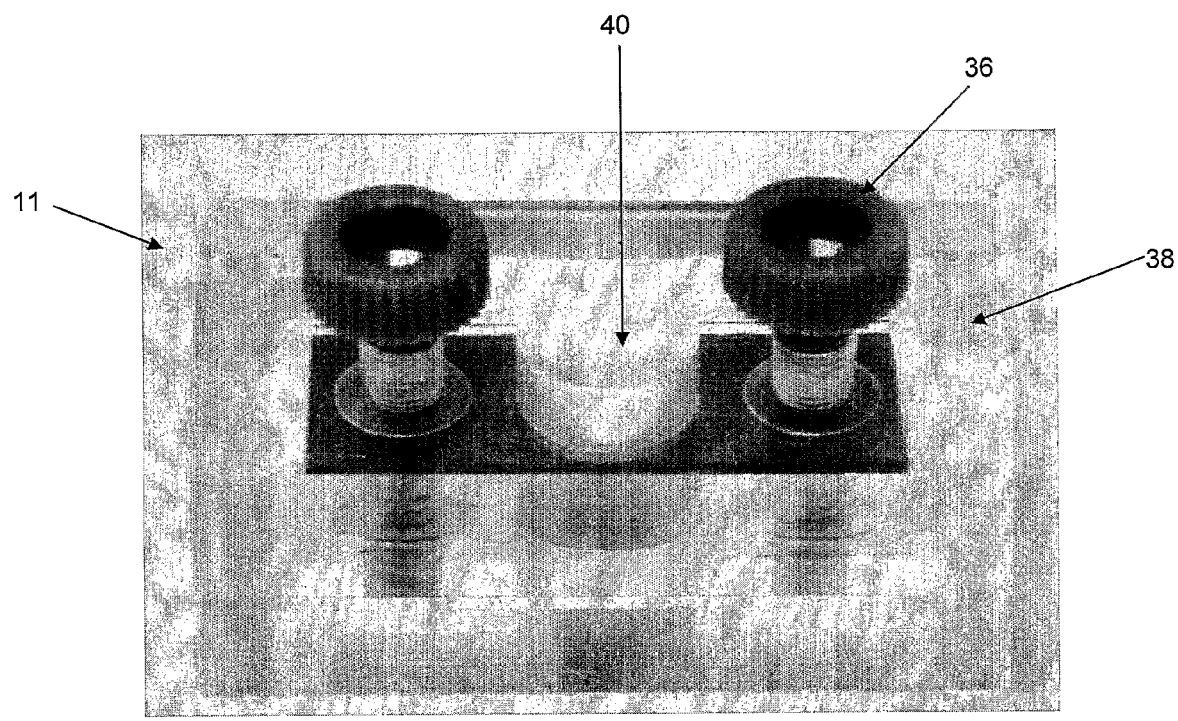
FIG. 3 is a picture of a prototype of an assembly of the sensor chip as disclosed herein.

Referring now to FIG. 2a, FIG. 2b and FIG. 3, there is shown an assembly 11 of the micro/nanofluidic sensor chip 10 as depicted in FIG. 1a. The assembly has a number of technical features that are the same as the micro/nanofluidic sensor chip 10 described above which are indicated by the same reference numeral but with a prime symbol (').

As shown in FIG. 2a, the assembly 11, further comprises two fittings 36 connected to two gaskets 30, which in turn are attached to the glass layer 12'. The fittings 36 are held together with the micro/nanofluidic device 10 by an pair of assembly jigs (38A, 38B). Tubings (34A, 34B) are inserted in fittings 36 to provide a connection to the inlet and outlet channels 18' and 22' respectively. The gasket 30 serves to prevent unwanted particles or dust from entering the micro/nanofluidic sensor chip 10 and also to prevent leakage of the fluid sample entering or exiting micro/nanofluidic sensor chip 10. In FIG. 2b, there is shown an alternate arrangement of the assembly 11 as depicted in FIG. 2a. Instead of having the tubings (34A, 34B) inserted from the top of the jig 38B, the tubings (34A, 34B) are inserted from the sides of the jig 38B.

When in use, a fluid sample of interest is passed through the tubing 34A and the fluid sample enters the inlet channel 18'. The fluid sample then flows over the gold nanostructures 28' which contain compounds that can bind to the target analytes that may be present in the fluid sample. An incident light 40, passes through the channel 20' at an incident angle and illuminates the nanostructures 28' to produce an LSPR signal associated with the constituents of the fluid sample. The LSPR signal is then detected from the light intensity profile of the light beam transmitted through the nanostructures, by a spectrometer (not shown). From the data obtained from the spectrometer, the shift of the LSPR extinction peaks in transmission relates to the refractive index change of the adjacent medium of the nanostructures. The wavelength range of the spectrometer for LSPR spectra scan is preferred to be 200-3000 nm for a full wavelength scan of the LSPR spectrum, or 400-900 nm for real applications as 400-900 nm wavelength range spectrometer is more cost effective. Because the wavelength of the LSPR extinction peak is tunable based on the size and the shape of the nanostructures, it can always be adjusted into the 400-900 nm range by nanostructure optimizations. Since LSPR might be sensitive to polarization of the light depending on the shape of the nanostructures, a linear polarizer (not shown) can be added in front of the beam that is incident onto the nanostructures. The assembly 11 can be linked to a mini-pump (not shown) for flow of a fluid sample to the enclosed chamber. A second mini-pump (not shown) may be provided in the outlet channel 22' to remove fluid sample from the enclosed chamber 23'. The removed fluid sample may have a decreased concentration of an analyte that may have reacted or have been bound to a target compound disposed on the nanostructures 28'. FIG. 3 shows a prototype of assembly 11 as depicted in FIG. 2a.

Figure 4:
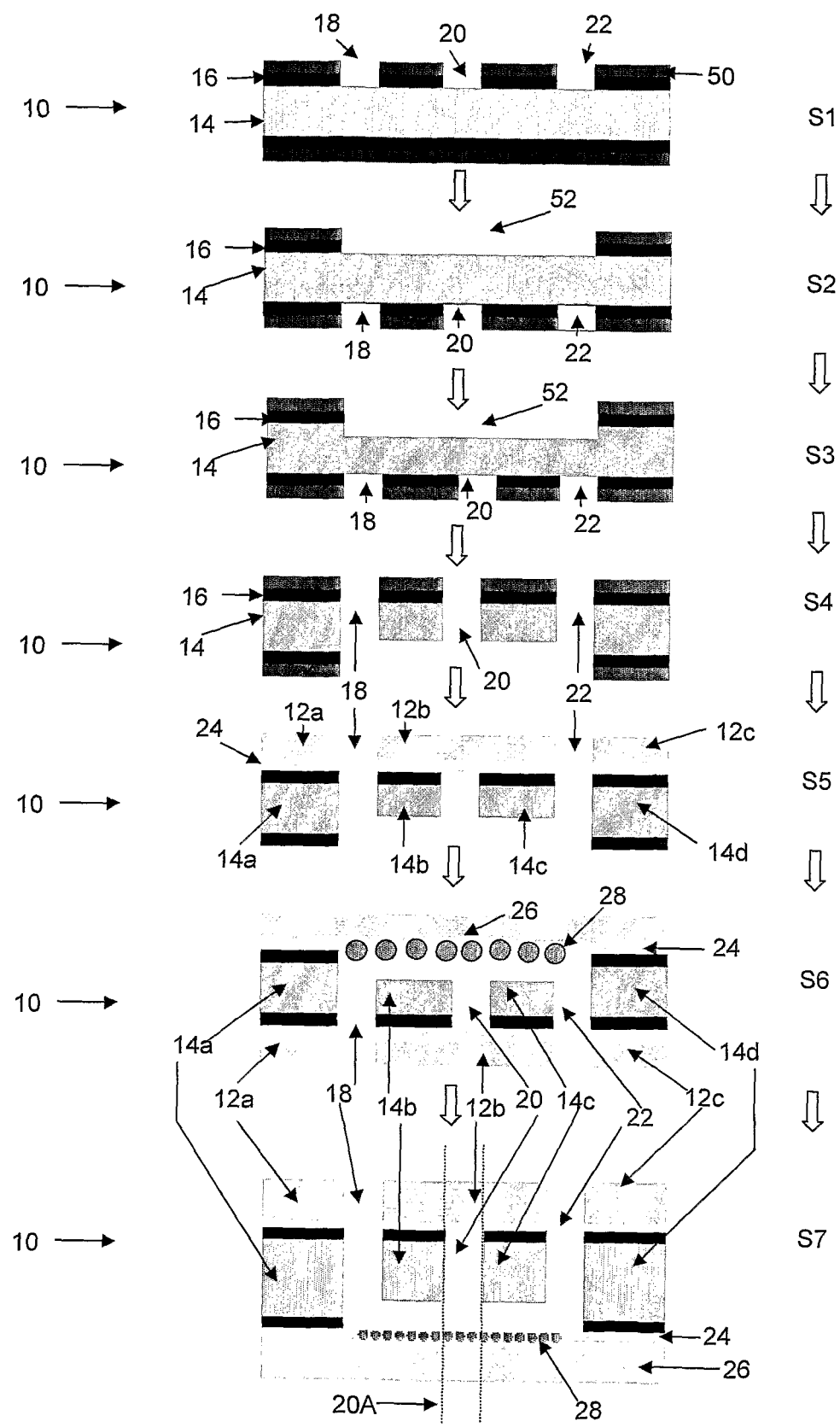
FIG. 4 is a flow diagram showing the steps taken to make the sensor chip as disclosed herein.

Referring now to FIG. 4, there is provided a flow diagram illustrating the steps taken to make the sensor chip 10 as disclosed above. The sensor chip 10 as mentioned above is made of Silicon and Pyrex 7740 glass through microfabrication technology. Here, a microfluidic sensor chip is made. The fabrication process starts from a standard RCA cleaning of a 4 inch (~100 mm) silicon wafer 14 with a thickness of 400 µm. After which, a 1 µm thick silicon dioxide layer 16 is deposited by Plasma Enhanced Chemical Vapor Deposition (PECVD) on both sides of the silicon wafer 14.

As shown in S1 of FIG. 4, the silicon wafer 14 is then spin coated with a layer of AZ4620 photoresist 50 on both sides. The silicon wafer 14 is subsequently exposed at 7 mW/cm$^2$ for 13 s and developed with AZ developer that obtained from Clariant Corporation, for 45 s to open the windows of inlet 18, outlet 22 and the transparent channel portion 20 which is part of the optical or light path 20A. The silicon dioxide 16 is etched by buffered oxide etch solution manufactured by Honeywell (containing NH$_4$F and HF at a volume ratio of 7:1) at an etch rate of 850 Å/min.

A microchannel 52 of 100 µm wide is then patterned on the other side of the wafer by photoresist coating, exposure, developing and oxide removal as shown in S2.

The microchannel 52 is then further etched to a depth of 50 µm using Deep Reactive-Ion Etching (DRIE) as shown in S3.

Following that, the inlet 18, outlet 22 and transparent channel portion 20 are etched through by Deep Reactive-Ion Etching (DRIE) to connect with the fluid path of the microchannel 52 as shown in S4. This silicon wafer 14 is diced into chips for the following bonding process as shown S5.

In the next step S5, a pyrex 7740 glass wafer 12 is diced into a chip 12a-12c with the same size as the silicon chip 14a-14d. The glass chip 12a-12c serves as the top cover of the microfluidic channel and is regarded as top glass chip. Inlet channel 18 and outlet channel 22 are then drilled in the top glass chip and Loctitte 3301 UV curable epoxy 24 with a refractive index of 1.48 is spin coated on the top glass chip. After aligning properly, the silicon chip and the top glass chip are bonded together and exposed under UV light at 7 mW/cm$^2$ (365 nm wavelength) for 5 min to cure the epoxy and form the bonding strongly.

A thin layer of gold nanostructures 28 is subsequently fabricated on another bottom pyrex 7740 glass chip 26 through nanosphere lithography (NSL) as depicted in S6. NSL is a powerful technique to inexpensively fabricate gold nanostructures 28 on the glass substrate 26 with controlled shape, size and interparticle spacing, and its fabricated nanostructures are suitable for LSPR sensing because of their tunability and varieties. A layer of Loctite 3301 UV curable epoxy 24 is then spin coated on the silicon surface of the previously bonded Si-glass structure, which is then carefully aligned to the bottom glass chip 26 with gold nanostructures 28 fabricated to bond them together. After UV exposure, the glass-silicon-glass sandwich-structure device is completed as shown in S7.

Figure 5A:
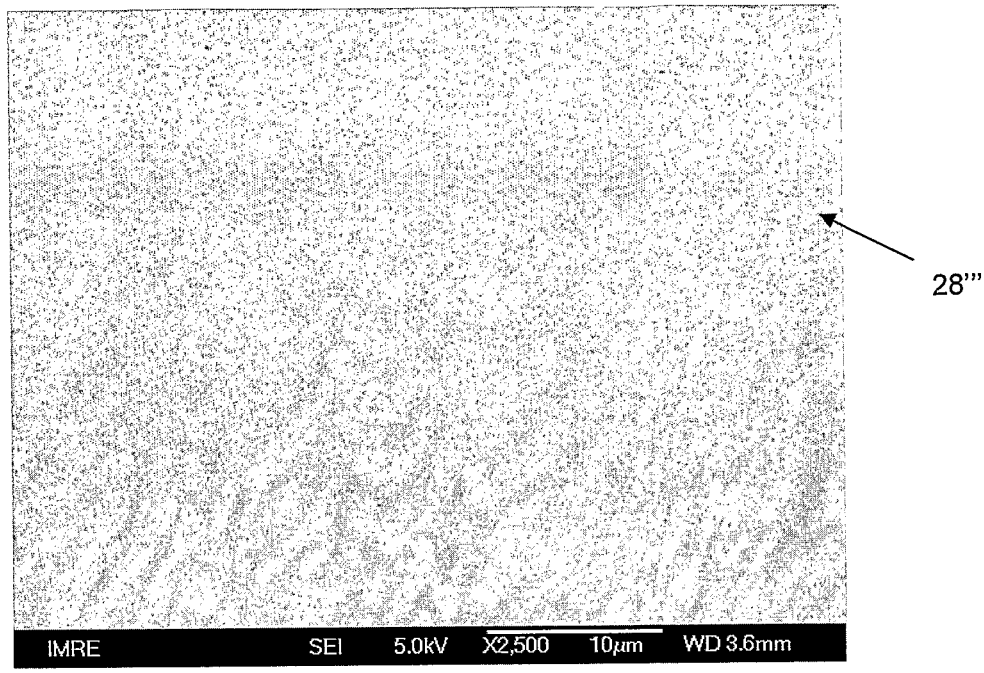
FIG. 5a and FIG. 5b are field emission scanning electron microscopy (FESEM) pictures of the nanostructures present in the sensor chip as disclosed herein.
Figure 5B:
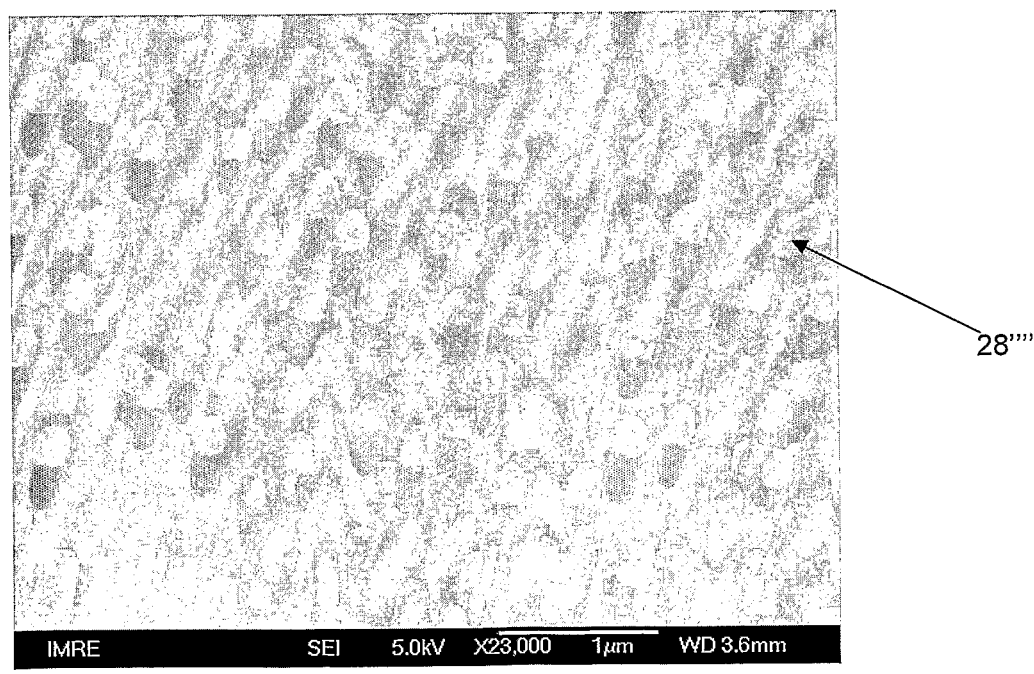

Referring to FIG. 5*a*, there is shown the FESEM picture of the nanostructures 28''' at 2500× magnification while FIG. 5*b* shows the FESEM picture of the nanostructures 28'''' at 23000× magnification. The figures show the discrete gold nanostructures 28'''/28'''' after the sensor chip 10 as disclosed above have been pried apart. It can be observed that the structural integrity of the gold nanostructures did not adversely change after carrying out the steps disclosed above to make the micro/nanofluidic sensor chip 10. This is indicative that the performance of the LSPR will not degrade when the aforementioned steps for making the micro/nanofluidic sensor chip 10 are used.

Figure 6A:
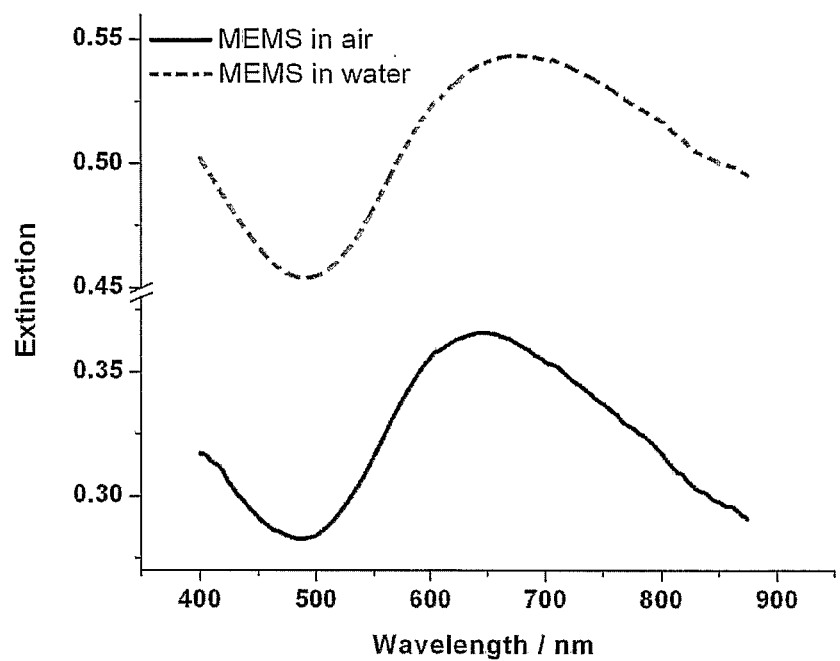
FIG. 6a and FIG. 6b are the LSPR spectra of the disclosed sensor chip measured with an Ocean Optics spectrometer.
Figure 6B:
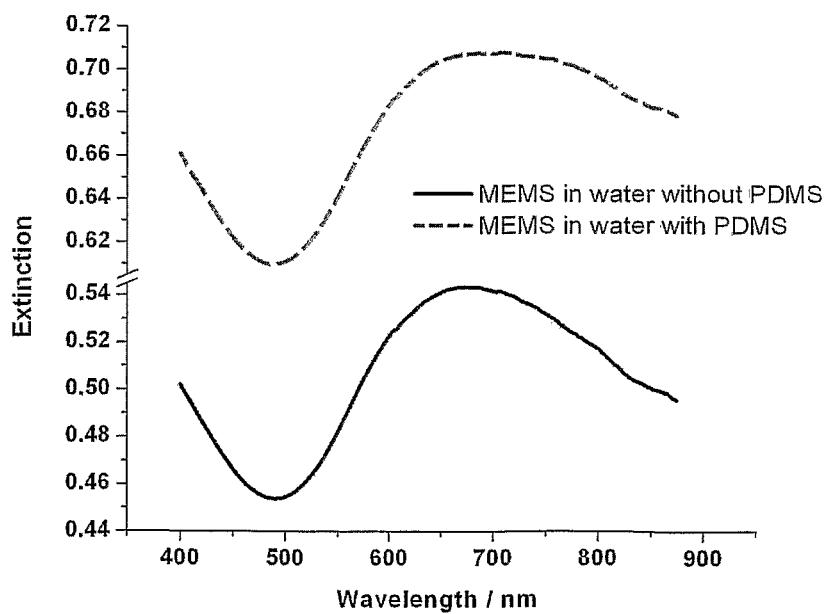

Referring to FIG. 6*a* and FIG. 6*b*, there is shown the LSPR spectra measurement results of the disclosed sensor chip with an Ocean Optics fiber optic spectrometer, composed of a DH2000 broadband source, a USB2000 spectrum detector (consists of a grating and a photodiode array) and optical fibers, which can well measure the spectra from 400-900 nm at an optical resolution of 0.35-0.36 nm. The light from the DH2000 light source of the spectrometer is coupled to the disclosed sensor chip with a fiber, after passing through the device, the light is re-coupled into another fiber that is connected with the USB3000 spectrum detector. FIG. 6*a* shows that the disclosed sensor chip functions well in sensing. It can be seen that for the disclosed sensor chip, when the adjacent medium changes from air to water (i.e., the refractive index changes from 1 to 1.33), the extinction peak of the LSPR spectra shifts from 642.16 nm to 677.35 nm, which is equivalent to a LSPR sensitivity of 106 nm/RIU, RIU is the unit of the refractive index. It should be noted that this sensitivity depends on the size, shape and the material of the nanostructures, and is not related with the micro/nanofluidic design.

FIG. 6*b* compares the LSPR spectra when a layer of 3 mm thick PDMS is added on the top of the disclosed sensor chip. The PDMS is transparent and allows light to be transmitted to the nanostructures. There is a spectrum broadening due to the addition of PDMS. From the experimental results provided in FIG. 6*b*, it can be seen that PDMS may still be used for the fabrication of the disclosed sensor chip. However, by comparing FIG. 6*b* and FIG. 6*a*, it can be observed that having glass as the top cover layer for the channel (FIG. 6*a*) results in a LSPR signal superior to one obtained when PDMS is being used as the transparent top layer. Moreover, PDMS is a porous material and it is not suitable for long term use in detecting biological samples because it tends to absorb some biological samples. For multiple use, it is believed that the residue in PDMS may also influence the accuracy of LSPR measurements adversely. In conclusion, although PDMS may be used as the transparent top cover layer for the sensor device, the silica based micro/nanofluidic device for LSPR application is most desirable in terms of durability, stability, reliability, repeatability and high optical transparency.

Experiments to Determine the Biological Sensing Function of the Sensor Chip

The following experiments were carried out using a glass sensor chip with gold nanostructures in accordance to one embodiment of the sensor chip disclosed herein. The glass sensor chip with gold nanostructures was fabricated by dispersing polystyrene nanospheres of 170 nm in diameter onto a glass substrate and subsequently evaporating 50 nm of gold film on the nanospheres.

In order to verify the biological sensing function of the LSPR device, two kinds of experiments were carried out. The first experiment was carried out using biotin-streptavidin complex which is a classic agent for investigating the specific bonding and real-time dynamic functions of SPR devices. The other experiment was carried out by determining bovine serum albumin (BSA) bonding to check the sensitivity compatibility of the LSPR device to a known device.

Experiment 1

Measurement of Biotin-Streptavidin Complex

LSPR spectra were taken by Ocean Optics spectroscopy. First, the spectrum was taken in air (as shown by the spectra labeled A in FIG. 7), then ethanol was added and the LSPR spectrum was taken (as shown by the spectra labeled B in FIG. 7) because the biotinylated thiol was in ethanol. 357 μM of biotinylated thiol (with 10 thiols attached with 1 biotin) was then injected and incubated at room temperature for 1 hour, rinsed with ethanol and the LSPR spectrum in ethanol was measured (as shown by the spectra labeled C in FIG. 7). Since streptavidin was in phosphate buffered saline (PBS), before adding the streptavidin, the medium was changed to PBS buffer and the LSPR spectrum was measured (as shown by the spectra labeled D in FIG. 7). Finally streptavidin at the concentration of 100 μg/ml was injected and incubated for 1 hour, rinsed with PBS and the LSPR spectrum was taken (as shown by the spectra labeled E in FIG. 7).

Figure 7:
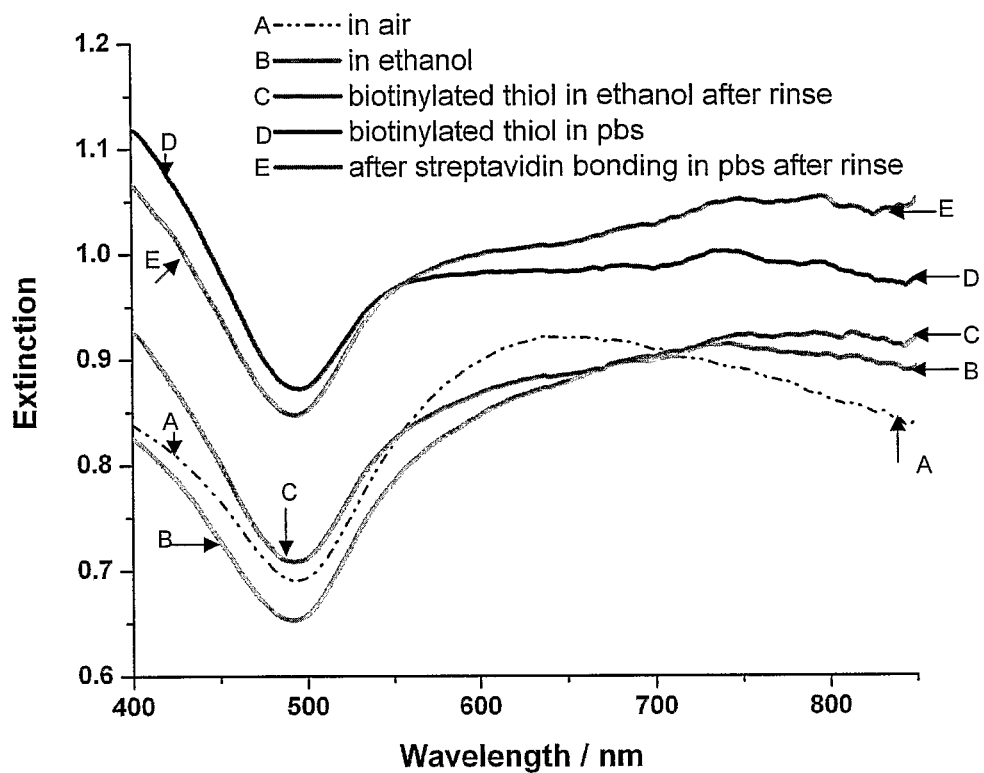
FIG. 7 shows the LSPR spectra of a glass sensor chip with gold nanostructures fabricated for biotin-streptavidin complex measurement in accordance to the experiments disclosed below.
Figure 8:
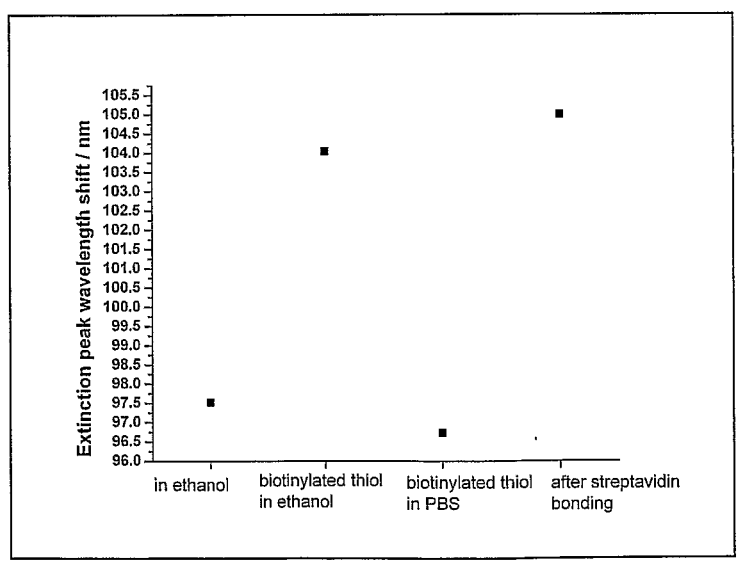
FIG. 8 shows the extinction peak wavelength shifts of the LSPR spectra of FIG. 7.

The extinction peak wavelengths of these LSPR measurements were 643.48, 741.01, 747.52, 740.21, and 748.47 nm, respectively, as shown in FIG. 7. The respective wavelength shifts are on the other hand shown in FIG. 8.

Because the refractive index of ethanol is 1.36, the LSPR wavelength shifted 97.53 nm (calculated by 741.01−643.48=97.53) in ethanol, indicating that the sensitivity of the LSPR chip was 270.91 nm/RIU (calculated by 97.53/(1.36−1)=270.91). The specific bond of biotin onto the gold nanostructures in ethanol caused a further wavelength shift of 6.51 nm (calculated by 747.52−741.01=6.51). When the medium was changed to PBS, the wavelength exhibited a decrease of 7.31 nm (calculated by 740.21−747.52=−7.31). This is because PBS has a lower refractive index compared with ethanol, which is 1.33467. This shift can be roughly expected by multiplying LSPR sensitivity of the sensor chip with the refractive index change, which is around 6.86 nm (calculated by 270.91×(1.36−1.33467)=6.86215). As will be apparent from the above, the calculated value of 6.86215 nm was very close the previous measured result of 7.31 nm, exhibiting relatively high predictability of the sensor chip.

When streptavidin was added, another wavelength shift of 8.26 nm after rinse indicated the specific bonding of streptavidin to biotin. Accordingly, the positive wavelength shift after streptavidin was added demonstrated that the sensor chip was responsive to the specific bonding of streptavidin to biotin and the biotin-streptavidin complex worked well with the sensor chip.

Experiment 2

Measurement of Bovine Serum Albumin (BSA)

LSPR spectra for bovine serum albumin (BSA) were measured by PerkinElmer spectroscopy. First a LSPR spectrum was taken in air (shown by the spectra labeled A in FIG. 9), subsequently 1 μg/ml phosphate buffered saline (PBS) buffer was added and the LSPR spectrum was taken (shown by the spectra labeled B in FIG. 9), and finally BSA was injected and incubated at room temperature for 1 hour, rinsed with PBS and the LSPR spectrum was measured (shown by the spectra labeled C in FIG. 9).

Figure 9:
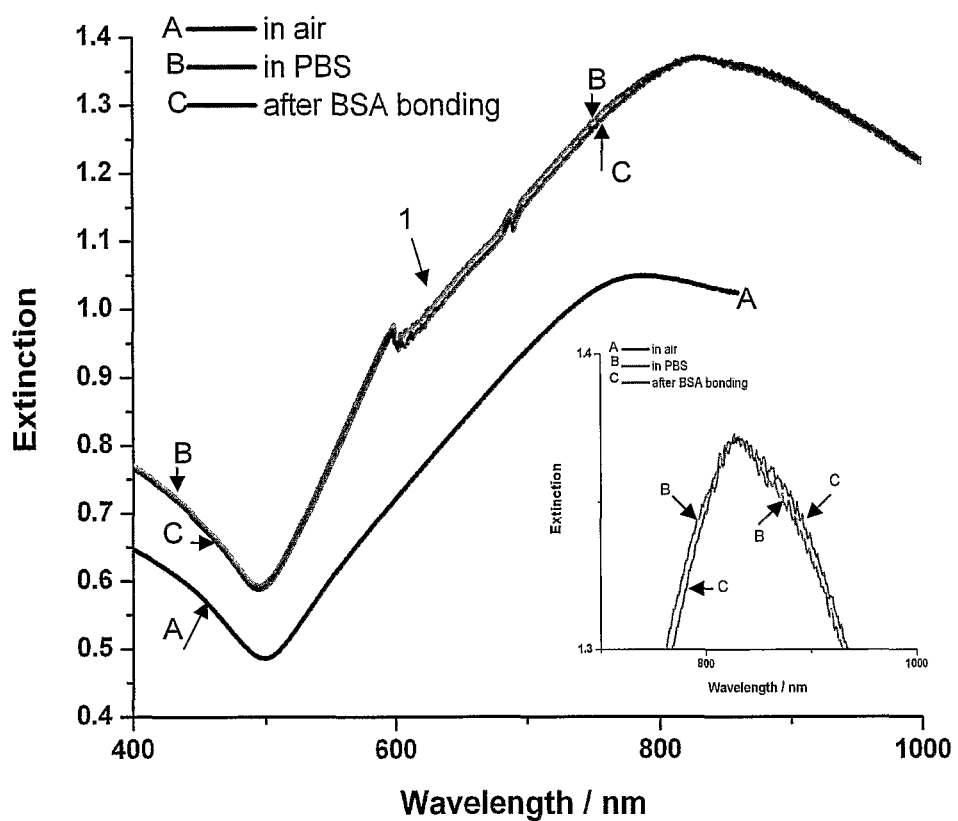
FIG. 9 shows the LSPR spectra of a glass sensor chip with gold nanostructures fabricated for BSA measurement in accordance to the experiments disclosed below.

The spectra of the experiment are shown in FIG. 9. The extinction peak wavelength of LSPR in air was 789 nm. As shown by arrow (1), BSA bonding shifts the spectrum of the PBS buffer slightly to the right, so it has to be discerned carefully. Since even in the insert (a magnification of spectra A and B) the peaks of the two LSPR spectra look close, the wavelength shift can be better identified by averaging the two wavelengths at the extinction intensity of 1.35, because at 1.35 this shift is discernable and is very close to the peak intensity of 1.37. For the PBS buffer, the left and right wavelengths at the intensity of 1.35 are respectively 798 and 873.5 nm. This renders a central wavelength of 835.75 nm. After BSA bonding, the left and right wavelengths at the intensity of 1.35 are respectively 802.5 and 881.5 nm. This gives a central wavelength of 842 nm.

The sensitivity of the LSPR chip was calculated to be 139.69 nm/RIU ((835.75−789)/(1.33467−1)=139.69). It should be noted that each LSPR chip has a different sensitivity due to the angle or thickness difference of the gold deposition. Based on the results above, the bonding of BSA caused the wavelength to red shift 6.25 nm (calculated by 842−835.75=6.25). Gao et al[1] also measured the wavelength shift of a LSPR chip with BSA bonding. However in Gao et al, the chip was first immersed in BSA and rinsed by PBS, then dried and measured in air. With the chip sensitivity of 110 nm/RIU, Gao et al detected a 7 nm shift in air.

The sensor chip in this present experiment had higher sensitivity of 139.69 nm/RIU, thus by proportion, if the present sensor chip is dried in air, a wavelength shift caused by BSA bonding is expected to be 8.89 nm (7×139.69/110=8.889). Moreover, because in the present experiment, the LSPR measurement for BSA was taken in PBS buffer, while the sensitivity of SPR or LSPR should also be further adjusted and be lowered by a factor close to the ratio of the refractive indices of air and the liquid, such that the expected LSPR wavelength shift in the present experiment is 6.66 nm (calculated by 8.889/1.33467=6.66). This expected value of wavelength shift through a series of normalization of the values obtained in Gao et al is very close to what was actually obtained experimentally, i.e. the experimental spectra shift was 6.25 nm.

The biological results indicate that the sensitivity and the function of the sensor chip is comparable in performance to device of the literature (Gao et al). However, the sensor chip disclosed herein is compact and has a simpler and effective design compared to the device of the literature and hence may be more easily manufactured on an industrial scale.

Experiment to Determine Signal Enhancement by Light Blockage

This experiment serves to show the effect of restricting the amount of light reaching the LSPR measurement device.

Gold nanostructures were fabricated on the substrate of the sensor chip in accordance with one embodiment disclosed herein, without the presence of a non-transparent element surrounding at least a portion of the optical path of a light beam transmitted through the sensor chip. The LSPR spectrum for the sensor chip was then measured.

Figure 10A:
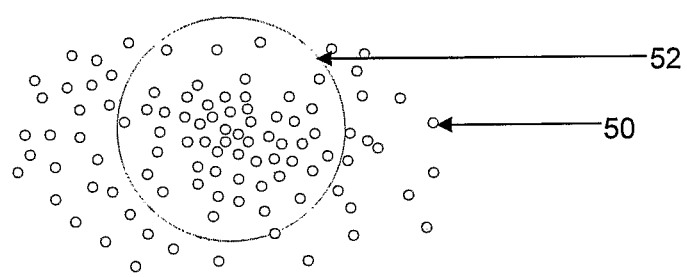
FIG. 10A and FIG. 10B are pictorial representations of sensor chips without and with non-transparent metal layer blockage respectively as described in the experiments disclosed below.
Figure 10B:
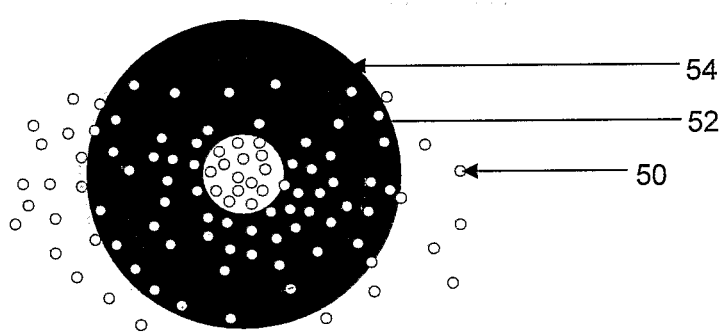
Figure 11A:
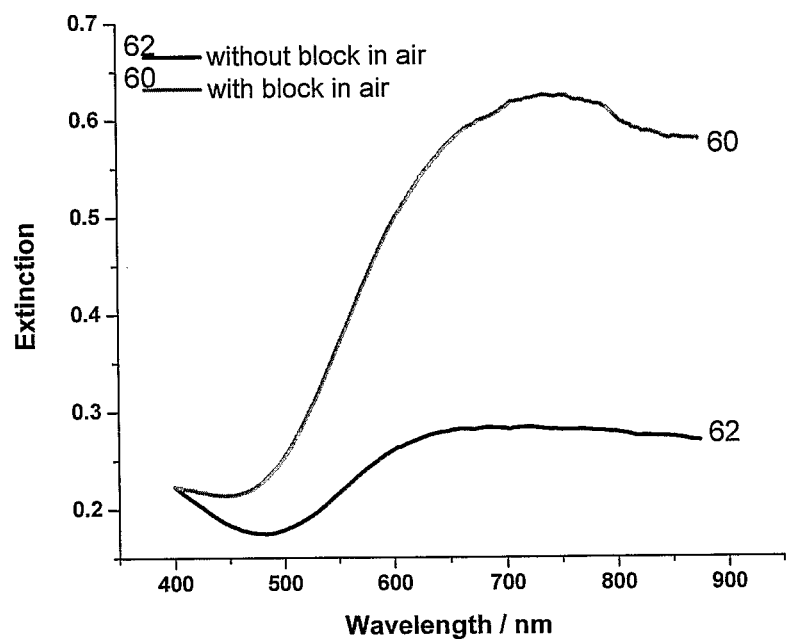
FIG. 11A-11D shows the LSPR spectra taken when with and without light blockage by non-transparent metal layer as described in the experiments disclosed below.
Figure 11B:
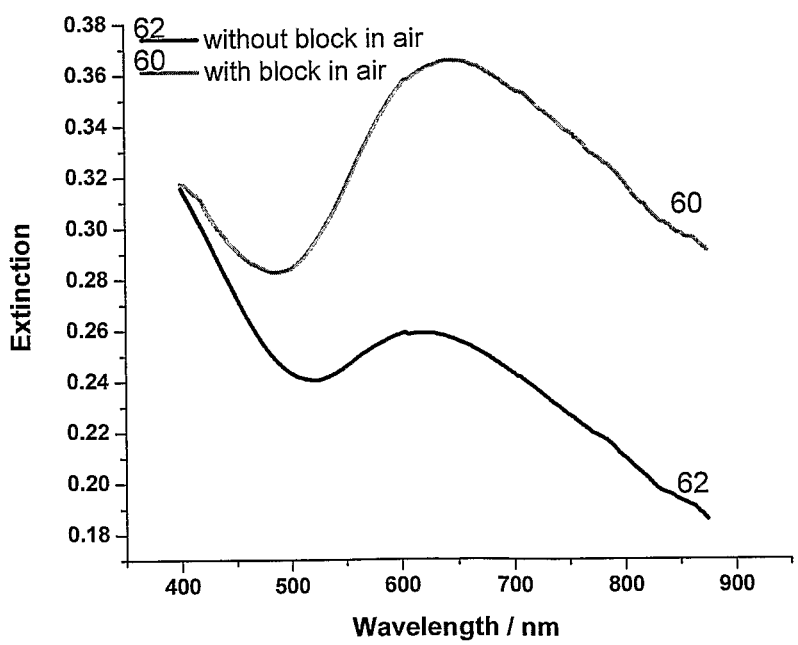
Figure 11C:
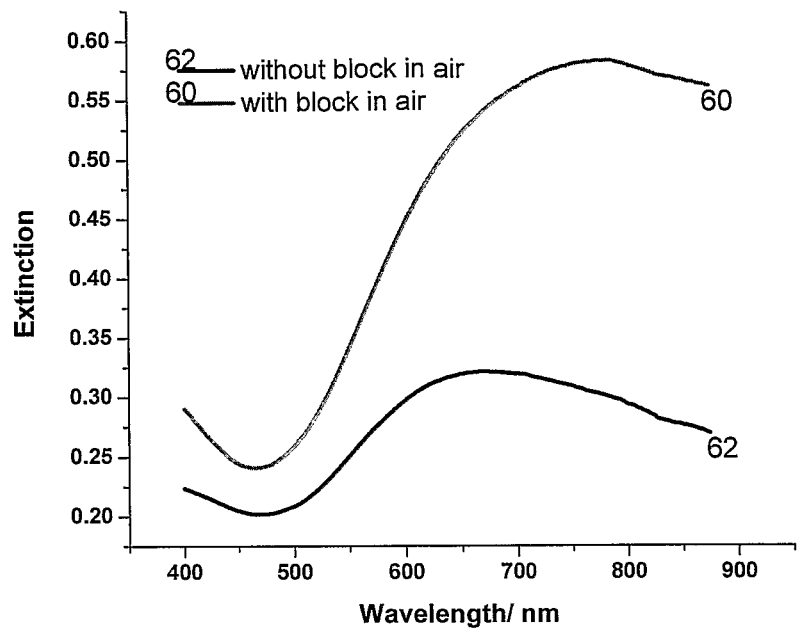
Figure 11D:
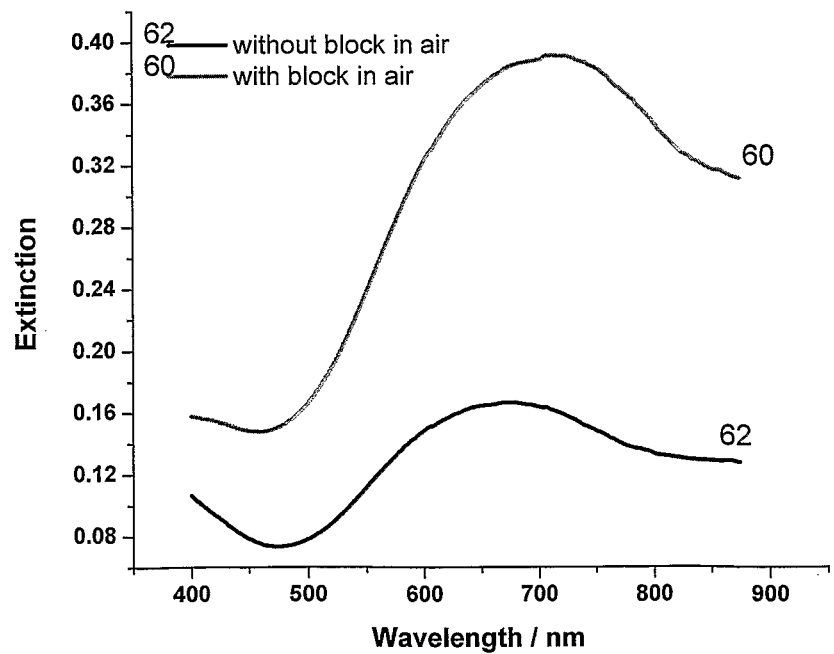

The sensor chip was then blocked with a non-transparent metal layer as disclosed in one embodiment herein, to partially block off the amount of light reaching the spectrometer. The LSPR spectrum for this sensor chip was then measured. FIG. 10A shows a pictorial representation of a sensor chip without a non-transparent element, viewed from the position of the spectrometer. FIG. 10B shows a pictorial representation of the sensor chip with non-transparent metal layer, viewed from the position of the spectrometer. The numerous small circles 50 represent the gold nanoparticles. The circular line 52 indicates the size of the light spot of the spectrometer. The shaded area 54 represents areas where light has been blocked by the metal layer.

The above experiment was carried out four times with four sensor chips and the spectra for the four different sensor chips were measured and presented in FIGS. 11A-11D. Spectra 62 represent the spectra obtained for the sensor chip that does not have a non-transparent element partially blocking off light reaching the spectrometer while spectra 60 represent the spectra obtained for the sensor chip that has non-transparent metal layer partially blocking off light reaching the spectrometer.

The results in FIGS. 11A-11D exhibit that the light blockage makes the peaks of the spectra prominent. This may be due to the fact that the gold nanostructures are more evenly distributed in a smaller area (less than 1 mm in diameter) than a large area of the whole light spot (about 5 mm in diameter).

APPLICATIONS

The disclosed sensor chip is an ultra-sensitive device for LSPR measurements and has precise control over ultra-small amount of sample fluid (nano liter or even smaller). Advantageously, the disclosed sensor chip is low-cost, robust, biocompatible and capable of being mass-produced.

The disclosed sensor chip may be used for a variety of applications in pharmaceutical industries, research, medical diagnostic testing, detection of biologics or microorganisms for food safety or security purposes (such as bio-terrorism monitoring) or in environmental monitoring. These applications may comprise ligand screening, immunology, cell biology, signal transduction, chemical interactions and nucleotide-nucleotide, nucleotide-protein, protein-protein and protein-lipid interactions.

The disclosed sensor chip may be used as biosensors for in-situ, label free analysis of binding reactions.

The sensor chip may be used for detecting ultra thin rigid layer formation or removal, such as thin film deposition or growth of metals, inorganic, organic, bio-compounds or polymers at ambient or elevated pressures. The detection of rigid layer formation can be obtained at the surface of the nanostructures or at the interfacial layer between two fluid phases. The sample material may be adsorbed onto the surface of the nanostructures, deposited onto the surface via vapour deposition in vacuum or at ambient pressures, chemically bonded to the surface as a result of a chemical reaction occurring at the surface or as a result of electrostatic interaction.

Advantageously, as the disclosed sensor chip has a high sensitivity within its electromagnetic decay length of 5-15 nm, it is very suitable for monolayer molecular or short-chain DNA detections. More advantageously, the sensor chip can be accurately aligned and is capable of being further miniaturized for biosensor arrays.

As the sensor chip disclosed herein is made with material such as glass, it also has reduced unwanted light scattering, improved optical contrast of LSPR and better bonding of the different components of the LSPR sensor chip. Due to the use of a material such as UV curable epoxy to attach the different components of the device, the internal stress within the sensor chip is advantageously reduced. As a result, the durability of the sensor chip may be maximized and advantageously, the sensor chip may be able to withstand frequent handling.

The disclosed sensor chip is also capable of being used in an environmental monitoring system, a clinical diagnostic system, a biomedical analysis system and a bio-detection system.

The method disclosed herein to make the sensor chip is also an efficient and simple method which can be easily adopted for mass production. Advantageously, as the method disclosed herein is a low-temperature and low-pressure microfabrication method, the disclosed method will not damage the nanostructures contained within the sensor chip, which are required for the generation of LSPR. More advantageously, the disclosed method will not undesirably roughen the surface of the glass wafers. As a result, unwanted scatterings in the sensor chip, which would adversely affect the LSPR signals, will be minimized.

While reasonable efforts have been employed to describe equivalent embodiments of the present invention, it will be apparent to the person skilled in the art after reading the foregoing disclosure, that various other modifications and adaptations of the invention may be made therein without departing from the spirit and scope of the invention and it is intended that all such modifications and adaptations come within the scope of the appended claims.

REFERENCE

1. D. Gao, W. Chen, A. Mulchandani, and J. S. Schultz, Detection of tumor markers based on extinction spectra of visible light passing through gold nanoholes, Appl. Phys. Lett. 90, 073901 (2007)

The invention claimed is:

1. A sensor chip comprising:
   a micro/nanofluidic channel;
   at least one nanostructure provided in said channel along an optical path for the transmission of a light beam;
   a light transparent element disposed along the optical path and arranged to allow transmission of light onto said nanostructure; and
   a non-transparent element surrounding at least a portion of said optical path to at least partially reduce light scatter from the optical path.

2. A sensor chip as claimed in claim 1, comprising a second light transparent element disposed along the optical path and arranged to allow transmission of light that has passed said nanostructure.

3. A sensor chip as claimed in claim 1, wherein the non-transparent element forms at least part of the sidewalls of the micro/nanofluidic channel.

4. A sensor chip as claimed in claim 1, wherein the non-transparent element is provided in or adjacent to the base of the said micro/nanofluidic channel.

5. A sensor chip as claimed in claim 1, comprising a reflector arranged to reflect light that has passed over said nanostructures back toward the optical path.

6. A sensor chip as claimed in claim 1, wherein said light transparent element has a refractive index of 1.4 to 2.

7. A sensor chip as claimed in claim 6, wherein said refractive index is 1.45 to 1.55.

8. A sensor chip as claimed in claim 1, wherein said light transparent element is at least one of glass and polydimethysiloxane.

9. A sensor chip as claimed in claim 4, wherein said non-transparent element is a metal layer.

10. The sensor chip as claimed in claim 1, wherein the sidewalls of the micro/nanofluidic channel comprise a layer of non-transparent silicon.

11. The sensor chip as claimed in claim 1, wherein the sidewalls comprise a layer of non-transparent silicon disposed between a layer of silicon dioxide and a transparent layer of glass.

12. The sensor chip as claimed in claim 8, wherein the glass comprises from about 60% wt to about 99% weight of silica.

13. The sensor chip as claimed in claim 8, wherein the glass is doped with from 1% weight to 40% weight of metal.

14. The sensor chip as claimed in claim 13, wherein the metal is selected from the group consisting of sodium, magnesium, calcium, lead, lanthanum, boron, thorium, cerium, antimony and mixtures thereof.

15. The sensor chip as claimed in claim 1, wherein said at least one nanostructure is a metal selected from the group consisting of gold, aluminum, cobalt, indium, molybdnenum, nickel, palladium, platinum, tin, titanium, tungsten, zinc, silver, copper and combinations thereof.

16. The sensor chip as claimed in claim 1, wherein a plurality of nanostructures is provided in said channel.

17. The sensor chip as claimed in claim 1, wherein said channel has at least one dimension of from about 10 nanometers to about 1500 microns.

18. The sensor chip as claimed in claim 1, wherein said channel is coupled to at least one inlet for transmission of a fluid sample into said channel and at least one outlet for transmission of said fluid from said channel.

* * * * *